US006918693B2

United States Patent
Ota et al.

(10) Patent No.: US 6,918,693 B2
(45) Date of Patent: Jul. 19, 2005

(54) LIGHT SOURCE DEVICE FOR ENDOSCOPE AND ASSEMBLY METHOD FOR LIGHT SOURCE UNIT

(75) Inventors: Noriko Ota, Saitama (JP); Takashi Sato, Saitama (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/367,774

(22) Filed: Feb. 19, 2003

(65) Prior Publication Data

US 2003/0156430 A1 Aug. 21, 2003

(30) Foreign Application Priority Data

Feb. 20, 2002 (JP) ........................................ 2002-042824

(51) Int. Cl.$^7$ ................................................. A61B 6/04
(52) U.S. Cl. ........................ 362/574; 362/555; 362/241; 362/346
(58) Field of Search ................................. 362/551, 554, 362/555, 800, 574, 572, 227, 235, 236, 238, 241, 320, 346

(56) References Cited

U.S. PATENT DOCUMENTS

| 5,585,783 | A | * | 12/1996 | Hall | ........................... | 340/473 |
|---|---|---|---|---|---|---|
| 5,864,642 | A | * | 1/1999 | Chun et al. | .................... | 385/14 |
| 6,260,994 | B1 | * | 7/2001 | Matsumoto et al. | ........ | 362/574 |
| 6,318,887 | B1 | * | 11/2001 | Matsumoto | ................. | 362/574 |
| 6,402,339 | B1 | * | 6/2002 | Mukogawa et al. | ........ | 362/184 |
| 6,438,302 | B1 | * | 8/2002 | Utsui et al. | ................. | 385/117 |
| 2002/0022766 | A1 | * | 2/2002 | Adachi | ....................... | 600/160 |
| 2002/0132108 | A1 | * | 9/2002 | Ikegawa et al. | ............ | 428/323 |

FOREIGN PATENT DOCUMENTS

JP          11216114          8/1999

* cited by examiner

Primary Examiner—Sandra O'Shea
Assistant Examiner—Hargobind S. Sawhney
(74) Attorney, Agent, or Firm—Greenblum & Bernstein, P.L.C.

(57) ABSTRACT

A light source device for an endoscope is provided. The light source device comprises a light source unit that supplies illumination light to an incident end face of a light guide member, which is laid inside an endoscope. The light source unit comprises a plurality of reflecting board members. Each reflecting board member has at least one light emitting diode. The plurality of reflecting board members are assembled into a concaved open polyhedron, so that the light emitted from the light emitting diodes are concentrated onto the incident end face of the light guide member.

16 Claims, 5 Drawing Sheets

LIGHT SOURCE DEVICE FOR ENDOSCOPE AND ASSEMBLY METHOD FOR LIGHT SOURCE UNIT

BACKGROUND OF THE INVENTION

1. Field of the Invention

The present invention relates to a light source device for an endoscope.

2. Description of the Related Art

An endoscope comprises an insertion portion that is inserted into a digestive organ of a human body and the like. From the distal end of the insertion portion, illumination light is emitted. A light guide which is comprised of glass fibers is inside the endoscope. One end of the light guide is optically connected to a light source of an exclusive light source device. The other end of the light guide is positioned at the distal end of the insertion portion. Although a xenon lamp, a halogen lamp, and so forth are generally used for the light source, in recent years, light emitting diodes or LEDs may be utilized as the light source.

An LED has superior characteristics, such as a miniature size, a small amount of wasted electricity, and little heat generation. However, an LED is inferior in terms of the amount of luminescence and beam spread.

SUMMARY OF THE INVENTION

An object of the present invention is to provide a light source unit for an endoscope that can be assembled in a simple manner.

According to the present invention, a light source device for an endoscope is provided that comprises a light source unit that supplies illumination light to an incident end face of a light guide member which is inside the endoscope.

The light source unit is an assembly of a plurality of reflecting board members that have light reflecting sides, and each of the plurality of reflecting board members comprises at least one light emitting diode.

Further, according to the present invention, a method for fabricating a light source unit is provided that comprises following first to fifth steps.

The first step is to cutout a board member from synthetic resins. The board member is cutout so as to form a pre-assembly shape or a development for a concaved open polyhedron. The second step is to form a reflecting layer on one side of the board member. The third step is to mount a plurality of light emitting diodes onto the board member on the side on which the reflecting layer is formed. The forth step is to assemble the board member into the concave open polyhedron. The fifth step is to electrically wire the light emitting diodes from the side of the board member which is opposite to the reflecting layer.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
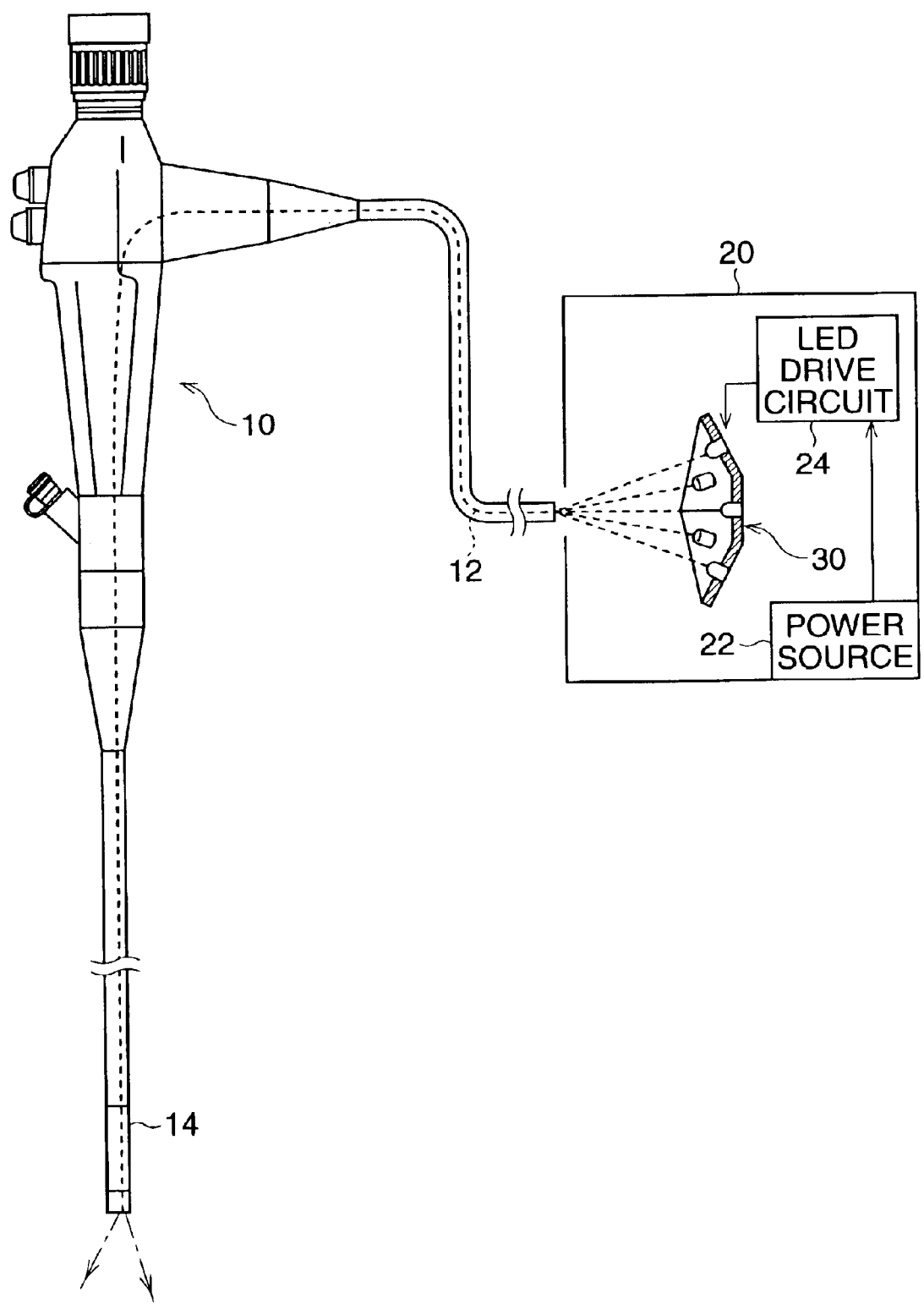
FIG. 1 illustrates a light source device of the present embodiment of the invention together with an endoscope.

The present invention is described below with reference to the embodiments shown in the drawings.

FIG. 1 illustrates a light source device of the present embodiment together with an endoscope. A light guide member 12 (indicated by a broken line in the figure) which is comprised of a plurality of glass fibers is inside the endoscope 10. One end of the light guide member 12 is optically connected to the light source unit 30 of the light source device 20, and the other end is positioned at the distal end of the insertion portion 14 of the endoscope. Note that, the light source unit 30 is arranged so that the center axis of the light source unit 30 coincides with the axis of the incident end face of the light guide member 12.

The light source device 20 comprises the light source unit 30 that includes a plurality of LED's which radiate white light, a power source 22 for supplying electric power to each LED, and an LED drive circuit 24 that controls the emission of each LED. Note that, in FIG. 1, although the LED drive circuit 24 is separated from the light source unit 30, the LED drive circuit 24 may be integrally built into the light source unit 30.

Figure 2:
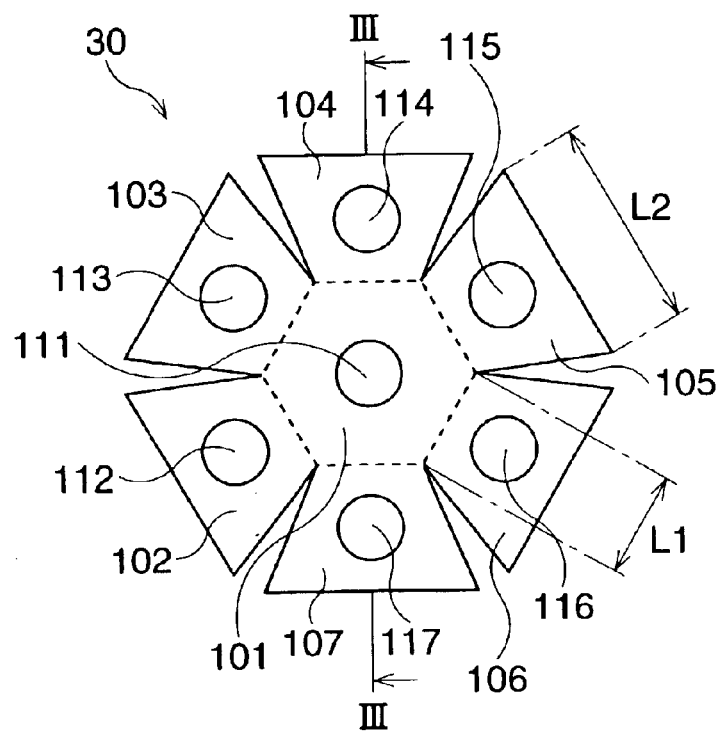
FIG. 2 is a pre-assembly shape or a development of the light source unit viewed from the side from which light is emitted.
Figure 3:
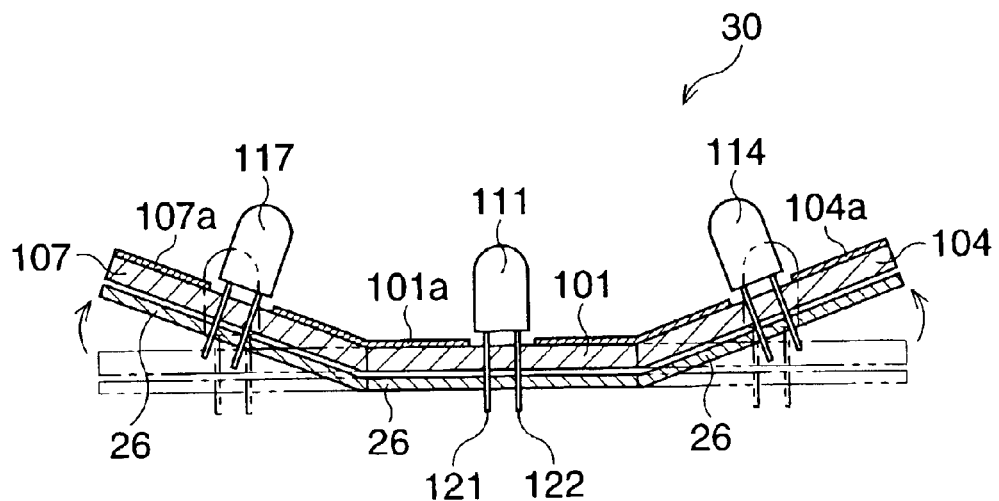
FIG. 3 shows a side view of the assembled light source unit along the line III—III in FIG. 2.

FIG. 2 is a pre-assembly shape or a development of the light source unit 30 viewed from the side from which light is emitted. FIG. 3 shows a side view of the assembled light source unit 30 along the line III—III in FIG. 2. The light source unit 30 may comprise seven reflecting board members 101, 102, 103, 104, 105, 106, and 107. Each of the reflecting board members 101 to 107 is comprised of a flat plate, and the light source unit 30 is an assembly of the reflecting board members 101–107. The first reflecting board member 101 that is positioned at the center of the unit 30 is formed as a regular hexagon shape with the side length L1. Each of the remaining six reflecting board members, or the second to seventh reflecting board members 102 to 107, is connected to each side of the first reflecting board member 101. Each reflecting board member 102–107 has an equivalent trapezoid shape with respect to one another. A top side (upper base) length of the each of the second to seventh reflecting board members 102–107 is equal to the side length L1 of the first reflecting board member 101. A bottom side (lower base) length L2 of each of the second to seventh reflecting board members 102–107 is defined in consideration of the inclined angle of each of the assembled second to seventh reflecting board members 102–107 with respect to the first reflecting board member 101. Note that, the inclined angle of each of the second to seventh reflecting board members 102–107 is defined in accordance with distance between the incident end face of the light guide member 12 and the light source unit 30, so that the entire light from the LED's is concentrated on the incident end face of the light guide member 12 when the LED's are mounted on the unit in the manner detailed afterward.

The first to seventh reflecting board members 101–107 may comprise synthetic resins. One side of each of the reflecting board members 101–107 is formed with a reflecting layer 101a–107a by a plating process or the like. Note that, in FIG. 3, only the reflecting layers 101a, 104a, and 107a are shown. At the substantially the center of each of the reflecting board members 101–107, LED's 111, 112, 113, 114, 115, 116, and 117 are respectively disposed.

For representative purposes, the first LED 111 will be detailed. The first LED 111 may be a bullet shaped LED. A pair of lead wires 121 and 122 penetrates the first reflecting board member 101 from the side of the reflecting layer 101a to the opposite side. The reflecting layer 101a is not formed on the area where the lead wires 121 and 122 of the LED penetrate the reflecting board member 101, so that the short circuit between the lead wires 121 and 122 is prevented. On the surface of the first reflecting board member 101 that is opposite to the reflecting layer 101a, the lead wires 121 and 122 of LED 111 are electrically connected to a flexible printed circuit 26, by a solder process for example, and the flexible printed circuit 26 is electrically connected to the LED drive circuit 24. The same is true with the second to seventh LED's 112–117, which are mounted on the second to seventh reflecting board members 102–107, respectively.

A fabrication method for the light source unit 30 will be described in the following. In the first process, a board member having a shape shown in FIG. 2 is cut from a synthetic resin board, and grooves, to facilitate bending the board, are formed on the side from which light is emitted, at the positions indicated with the broken lines in FIG. 2. In the second process, the cutout synthetic resin board is subjected to a plating process except in the areas where the LED lead wires penetrate the board, so that the reflecting layers 101a to 107a are formed. In the third process, the first to seventh LED's 111–117 are mounted onto the reflecting layer surface of the synthetic resin board. The synthetic resin board is bent at the grooves cut into the board, and adjacent sides of each trapezoid are put together in the forth process, so that a concave open polyhedron shape is formed. In the fifth process, the lead wires of the LED's 111–117 and the flexible print circuit 26 are soldered together. Thereby, the LED's 111–117 are fixed to the corresponding reflecting board members 101–107, respectively, by means of soldering processes.

As described above, since the light source unit 30 of the present embodiment is formed from a substrate plate, the fabrication process is simplified. Particularly, the processes for mounting the LED's are made efficient. Further, the time for each process is reduced thus the cost is reduced.

Figure 4:
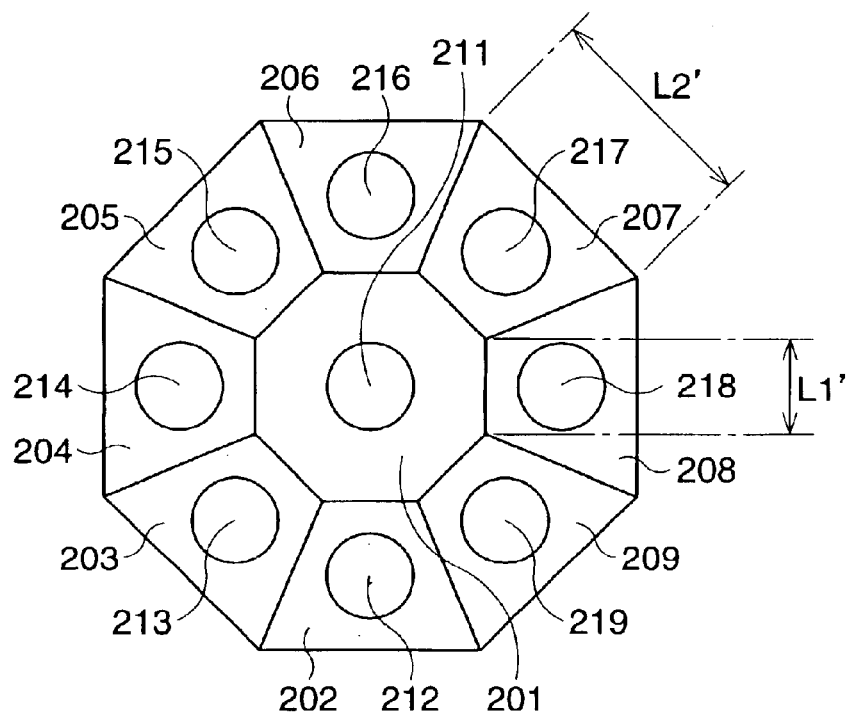
FIG. 4 is a plan view of another example of the light source unit.

The number of LED's and reflecting board members is not restricted to the present embodiment. For example, as shown in the plan view in FIG. 4, trapezoidal reflecting board members 202–209 may be arranged around an octagonal reflecting board member 201, and the LED's 211–219 may be mounted on reflecting board members 201–209, respectively. Note that here, L1' and L2', respectively designate the side length of the reflecting board member 201 and the bottom side length of the reflecting board members 202–209, and are determined so that the entire light from the LED's is concentrated on the incident end face of the light guide member 12 when the light source unit 30 is assembled and optically connected to the light guide member 12.

Figure 5:
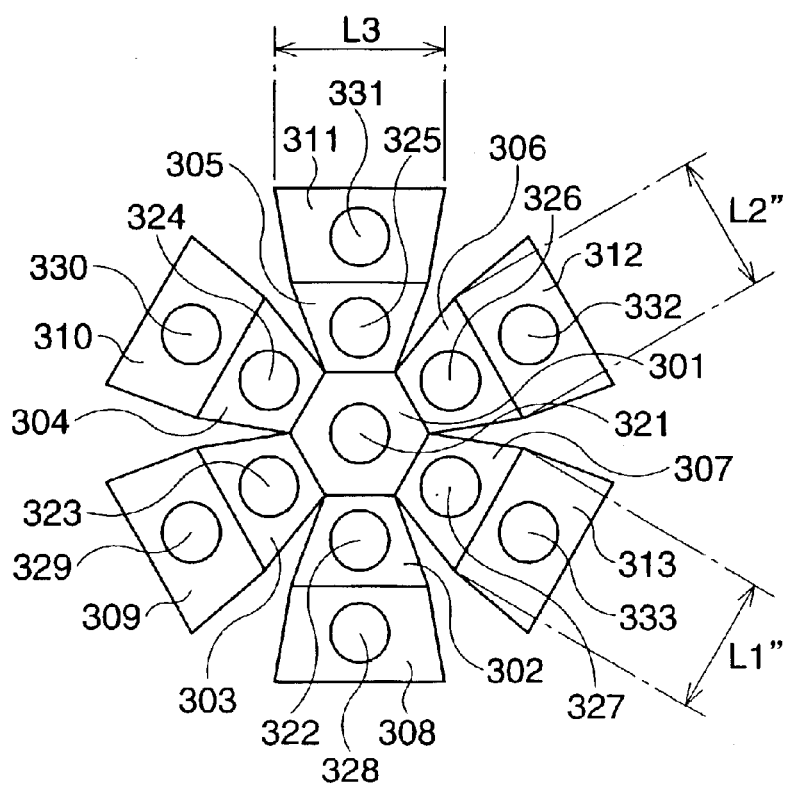
FIG. 5 is a pre-assembly shape or a development of another example of the light source unit.

Further, as shown in the pre–assembly structure or the development of FIG. 5, six reflecting board members 302–307 may be arranged around a hexagonal reflecting board member 301, and six trapezoidal reflecting board members 308–313 may be arranged radially around the outer side of each reflecting board member 302–307. Further, the LED's 321–333 may be mounted on the reflecting board members 301–313, respectively. Note that here, L1", L2", and L3, respectively designate the side length of the reflecting board member 301, the bottom side length of the reflecting board members 302–307, and the bottom side length of the reflecting board members 308–313, and are determined so that the entire light from the LED's is concentrated on the incident end face of the light guide member 12 when the light source unit 30 is assembled and optically connected to the light guide member 12.

In the present embodiment, although only one LED is mounted on one reflecting board member, a plurality of LED's may be mounted on a single reflecting board member. Further, in the present embodiment, a bullet shaped LED is used, however, the shape or type of an LED is not restricted to the one used in this embodiment, so that any other type of LED, such as a laminated-type LED or a chip-type LED, or the like, may be used. Further, in the present embodiment, all the LED's radiate white light, however, the same number of red, green, and blue colored LED's, which corresponds to the three color principle, may be arranged on the reflecting board members, so that the composite white light can be supplied to the end face of the light guide member by radiating the three light colors from the LED's simultaneously.

Further, in the present embodiment, although the reflecting layer is formed by a plating process, an aluminum film of which the surface is subject to an electric non-conductance process may be applied to the reflecting board members, so as to form the reflecting layer, other than in the areas where lead wires of the LEDs penetrate the reflecting board member.

Figure 6A:
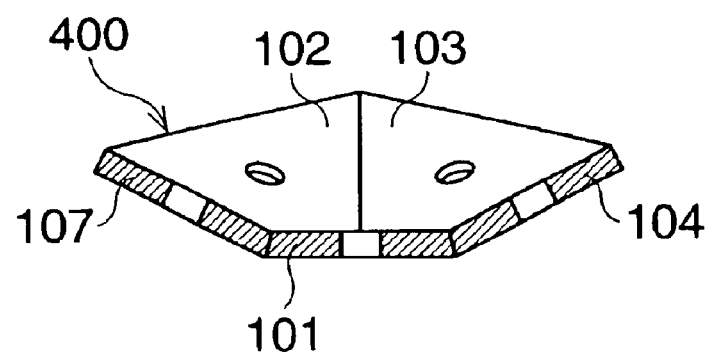
FIGS. 6A and 6B are a cross sectional side view of another example of light source unit which is fabricated in different processes.
Figure 6B:
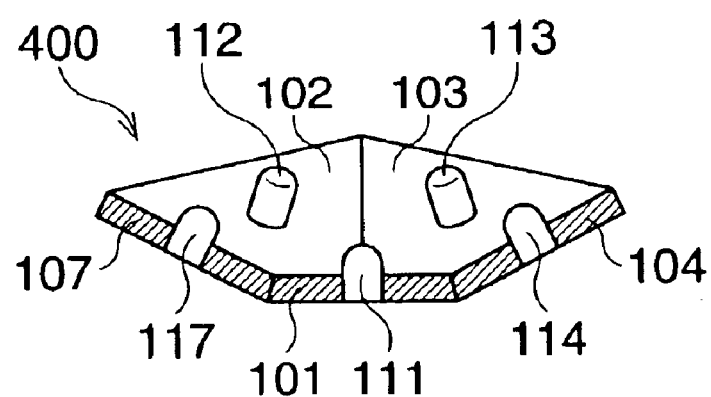

Furthermore, the fabrication process is not restricted to that in the present embodiment. As shown in FIG. 6A, a concave open polyhedron 400 may be integrally formed as a composition of seven reflecting board members 101–107 made of synthetic resin. Then the seven LED's may be respectively mounted on the reflecting board members 101–107 after a reflecting layer is plated on the inner surface of the concaved open polyhedron 400. Finally, a flexible printed circuit may be attached onto the outer surface of the concaved open polyhedron 400 for soldering each LED to the flexible printed circuit, as shown in FIG. 6B.

Figure 7A:
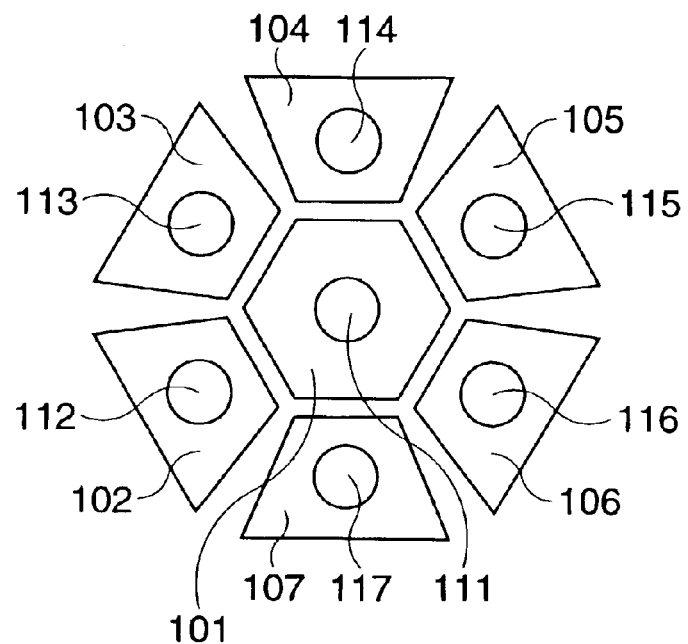
FIG. 7A is a plan view of another example of a light source unit which is fabricated in different processes.
Figure 7B:
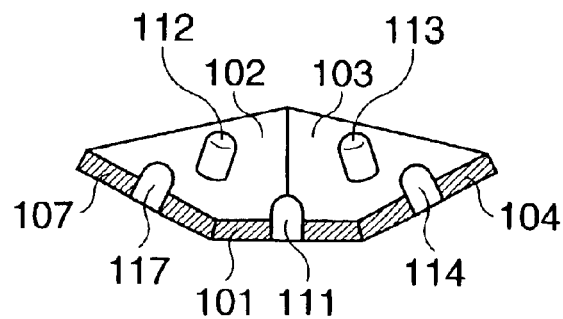
FIG. 7B is a cross sectional side view of the light source unit shown in FIG. 7A.

Further, as shown in FIG. 7A, the LED's 111–117 may be mounted on the reflecting board members 101–107 that are cutout from a synthetic resin board with one side having a reflecting layer. Then the reflecting board members 101–107 with the LED's 111–117 may be assembled into a concaved open polyhedron by putting each reflecting board member 101–107 together. Finally, a flexible printed circuit may be attached onto the outer surface of the concaved open polyhedron and each LED can be soldered to the flexible printed circuit, as shown in FIG. 7B.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2002-042824 (filed on Feb. 20, 2002) which is expressly incorporated herein, by reference, in its entirety.

What is claimed is:

1. A light source device for an endoscope, comprising:

a light source unit that supplies illumination light to an incident end face of a light guide member inside an endoscope, said light source unit is an assembly of a plurality of reflecting board members that have a light reflecting side, and each of said plurality of reflecting board members include a single bullet-shaped light emitting diode, the light emitted from said light emitting diodes is concentrated onto the incident end face of the light guide member, and wherein said assembly is arranged to form a concave open polyhedron shape.

2. The light source device according to claim 1, wherein said plurality of reflecting board members comprise a synthetic resin which has a reflecting layer on one side.

3. The light source device according to claim 2, wherein said reflecting layer comprises a plating.

4. The light source device according to claim 2, wherein said reflecting layer is not formed on an area where lead wires of each said light emitting diode penetrate said reflecting board member, so that a short circuit between said lead wires is prevented.

5. The light source device according to claim 1, further comprising a flexible printed circuit attached on each reflecting board member of said plurality of reflecting board members on a side opposite to said light reflecting side, to supply electrical power to each said light emitting diode.

6. A method for fabricating a light source unit comprising:

cutting a board member, of a synthetic resin, into a shape to form a concave open polyhedron shape;

forming a reflecting layer on one side of the board member;

mounting a plurality of light emitting diodes onto the board member on which the reflecting layer is formed;

assembling the board member into the concave open polyhedron shape; and wiring the light emitting diodes on a side of the board member which is opposite to the reflecting layer.

7. A light source device that supplies illumination light to an incident end face of a light guide member of an endoscope, the device comprising:

a plurality of trapezoid-shaped reflecting board members that have a light reflecting side, and each of said plurality of reflecting board members includes at least one light emitting diode, the light emitted from said light emitting diodes is concentrated onto the incident end face of the light guide member, and wherein said plurality of trapezoid-shaped reflecting board members are configured to form a bowl shape.

8. The light source device according to claim 7, wherein said plurality of reflecting board members include a synthetic resin which has a reflecting layer on one side.

9. The light source device according to claim 8, wherein said reflecting layer comprises a plating.

10. The light source device according to claim 8, wherein said reflecting layer is not formed on an area where lead wires of said at least one light emitting diode penetrate a respective reflecting board member, so that a short circuit between said lead wires is prevented.

11. The light source device according to claim 7, further comprising a flexible printed circuit which is attached on each reflecting board member of said plurality of reflecting board members on a side opposite to said light reflecting side, to supply electrical power to said at least one light emitting diode.

12. A light source device that supplies illumination light to an incident end face of a light guide member inside an endoscope, the device comprising:

a plurality of trapezoid-shaped reflecting board members that have a light reflecting side, each of said plurality of reflecting board members includes at least one light emitting diode, the light emitted from said light emitting diodes being concentrated onto the incident end face of the light guide member; and a center reflecting board member, wherein said plurality of trapezoid-shaped reflecting board members are attached to the center reflecting board member to form a polyhedron shape.

13. The light source device according to claim 12, wherein said plurality of reflecting board members and said center reflecting board member include a synthetic resin which has a reflecting layer on one side.

14. The light source device according to claim 13, wherein said reflecting layer comprises a plating.

15. The light source device according to claim 13, wherein said reflecting layer is not formed on an area where lead wires of said at least one light emitting diode penetrate a respective reflecting board member, so that a short circuit between said lead wires is prevented.

16. The light source device according to claim 12, further comprising a flexible printed circuit which is attached on each reflecting board member of said plurality of reflecting board members and said center reflecting board member on a side opposite to said light reflecting side, to supply electrical power to said at least one light emitting diode.

* * * * *